US012496445B2

(12) United States Patent
Cakmak

(10) Patent No.: US 12,496,445 B2
(45) Date of Patent: Dec. 16, 2025

(54) NON-INVASIVE STIMULATION SYSTEM FOR SYNCHRONOUS STIMULATION OF STERNOCLEIDOMASTOID MUSCLES AND CUTANEOUS CERVICAL NERVE BRANCHES WITH AUTONOMIC CONNECTIONS

(71) Applicant: Yusuf Ozgur Cakmak, Uskudar/Istanbul (AR)

(72) Inventor: Yusuf Ozgur Cakmak, Uskudar/Istanbul (AR)

( * ) Notice: Subject to any disclaimer, the term of this patent is extended or adjusted under 35 U.S.C. 154(b) by 648 days.

(21) Appl. No.: 17/842,221

(22) Filed: Jun. 16, 2022

(65) Prior Publication Data

US 2022/0313995 A1 Oct. 6, 2022

Related U.S. Application Data

(63) Continuation of application No. PCT/TR2019/051093, filed on Dec. 17, 2019.

(51) Int. Cl.
*A61N 1/36* (2006.01)
*A61N 1/04* (2006.01)

(52) U.S. Cl.
CPC ....... *A61N 1/36025* (2013.01); *A61N 1/0452* (2013.01); *A61N 1/0456* (2013.01); *A61N 1/36031* (2017.08)

(58) Field of Classification Search
CPC .............. A61N 1/36025; A61N 1/0452; A61N 1/0456; A61N 1/36031; A61N 2005/0626;
(Continued)

(56) References Cited

U.S. PATENT DOCUMENTS

2007/0073361 A1 3/2007 Goren et al.
2009/0187124 A1* 7/2009 Ludlow .................. A61H 23/00 601/47

(Continued)

FOREIGN PATENT DOCUMENTS

EP 2 524 717 A1 11/2021
WO WO-2012156052 A2 * 11/2012 ........... A61H 39/002

(Continued)

OTHER PUBLICATIONS

Rea, Paul, ed. Essential Clinically Applied Anatomy of the Peripheral Nervous System in the Head and Neck. Academic Press (2016). 213 pages.

(Continued)

*Primary Examiner* — James M Kish
*Assistant Examiner* — Natasha Patel
(74) *Attorney, Agent, or Firm* — Crowell & Moring LLP

(57) ABSTRACT

A stimulation device includes a body containing at least one stimulation means adapted to be transcutaneously attached to the neck of a subject. The stimulation means is adapted to generate a stimulating signal during a stimulating state. The stimulation means is positioned to be in stimulating contact with the sternocleidomastoid muscle and the trunks of the lesser occipital nerve, greater auricular nerve, transverse cervical nerve or supraclavicular nerve with their autonomic fibers synchronously. The stimulation can be provided in the form an electrical, optical, vibrational, thermal, mechanical and/or magnetic stimulation. The stimulation device can be used bilaterally on the right and left sides of the subject's neck, working as a system in a synchronous or alternating manner.

18 Claims, 2 Drawing Sheets

Figure 1:
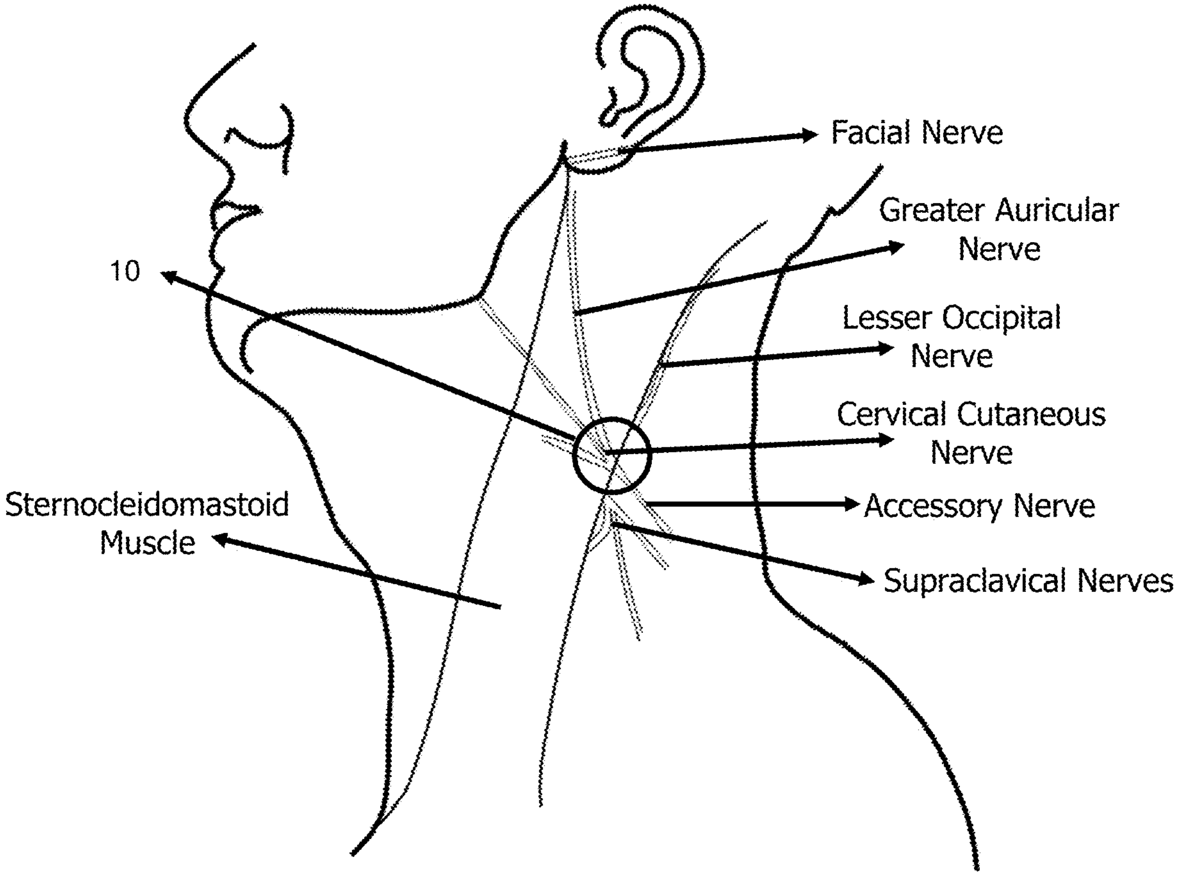

(58) Field of Classification Search
CPC .... A61N 2005/0645; A61N 2005/0659; A61N 2007/0026; A61N 1/0476; A61N 1/36021; A61N 1/37217; A61N 2/002; A61N 2/006; A61N 5/0622; A61B 5/0077; A61B 5/02405; A61B 5/02416; A61B 5/02438; A61B 2562/0204; A61B 2562/0219; A61B 2562/0233; A61B 2562/0271; A61B 5/01; A61B 5/0531; A61B 5/1103; A61B 5/1118; A61B 5/30; A61B 5/369; A61B 5/389; A61B 5/4803; A61B 5/4848; A61B 5/6822
See application file for complete search history.

(56) References Cited

U.S. PATENT DOCUMENTS

| | | | | |
|---|---|---|---|---|
| 2013/0225954 | A1 | 8/2013 | Ludlow et al. | |
| 2014/0236262 | A1 * | 8/2014 | You | A61B 8/08 607/59 |
| 2014/0379049 | A1 * | 12/2014 | Mashiach | A61B 5/682 607/60 |
| 2016/0151628 | A1 | 6/2016 | Simon et al. | |
| 2019/0001117 | A1 | 1/2019 | Ben-David et al. | |
| 2019/0046787 | A1 * | 2/2019 | Tyler | A61N 1/0492 |
| 2019/0159953 | A1 * | 5/2019 | Konczak | A61H 1/005 |
| 2019/0209841 | A1 | 7/2019 | Errico et al. | |
| 2019/0366076 | A1 * | 12/2019 | Simon | A61N 1/36025 |
| 2021/0138231 | A1 * | 5/2021 | Lindenthaler | A61N 1/0452 |
| 2021/0353943 | A1 | 11/2021 | Simon et al. | |
| 2022/0347471 | A1 | 11/2022 | Simon et al. | |

FOREIGN PATENT DOCUMENTS

| | | | |
|---|---|---|---|
| WO | WO 2015/179571 | A1 | 11/2015 |
| WO | WO-2021126097 | A1 | 6/2021 |

OTHER PUBLICATIONS

International Search Report and Written Opinion, dated Aug. 14, 2020, pp. 1-9, issued in International Patent Application PCT/TR2019/051093, European Patent Office, Rijswijk, The Netherlands.
Cakmak, Yusuf O., et al., "Rapid Alleviation of Parkinson's Disease Symptoms via Electrostimulation of Intrinsic Auricular Muscle Zones," Frontiers in Human Neuroscience, Clinical Trial, Published Jun. 28, 2017, doi: 10.3389/fnhum.2017.00338.
Bordoni, B., Varacallo, M., "Anatomy, Head and Neck, Sternocleidomastoid Muscle," dated Dec. 17, 2018, pp. 1-9, NCBI Bookshelf. A service of the National Library of Medicine, National Institutes of Health. StatPearls [Internet]. Treasure Island (FL): StatPearls Publishing; Jan. 2018. Bookshelf ID: NBK532881 PMID: 30422476 URL: https://www.researchgate.net/publication/329718352.
Waxenbaum JA, Reddy V, Bordoni B. "Anatomy, Head and Neck, Cervical Nerves." [Updated Jul. 21, 2021], pp 1-4.. In: StatPearls [Internet]. Treasure Island (FL): StatPearls Publishing; Jan. 2022.

* cited by examiner

NON-INVASIVE STIMULATION SYSTEM FOR SYNCHRONOUS STIMULATION OF STERNOCLEIDOMASTOID MUSCLES AND CUTANEOUS CERVICAL NERVE BRANCHES WITH AUTONOMIC CONNECTIONS

CROSS-REFERENCE TO RELATED APPLICATIONS

This application is a continuation of International Application No. PCT/TR2019/051093, filed Dec. 17, 2019, which designates the United Sates.

TECHNICAL FIELD

The present disclosure relates to a stimulation device and system capable of non-invasive and synchronous stimulation of sternocleidomastoid muscles and cutaneous cervical nerve branches (with their sympathetic nerve content) from a single location for alleviating both the motor and autonomic symptoms of and treatment of neurological conditions. The stimulation can be provided in the form an electrical stimulation and/or optic stimulation and/or a vibration and/or thermal and/or mechanical, and/or magnetic stimulation. The stimulation device can be used bilaterally on the right and left sides of the patient's neck, working as a system in a synchronous or alternating manner.

BACKGROUND

Abnormal resting over activity as tremors can be caused by various conditions or medicines that affect the nervous system, including Parkinson's disease (PD), liver failure, alcoholism, mercury or arsenic poisoning, lithium, and certain antidepressants. Rigidity, bradykinesia and postural instability are some of the other symptoms of the Parkinson's disease besides tremors. Parkinson's disease is a chronic and progressive movement disorder, meaning that symptoms continue and worsen over time. According to European Parkinson's Disease Association, it is estimated that 6.3 million people in the world are living with Parkinson's disease. The cause is unknown, and although there is presently no cure, there are treatment options such as medication and surgery to manage its symptoms. Stimulation of different parts of a brain with different techniques can be successfully used for the treatment of Parkinson's disease.

SUMMARY

The main objectives of the deep brain stimulation (DBS) devices are stimulation of the subthalamic nucleus and as a consequence, activation of the supplementary motor areas and premotor areas and normalization of the abnormal resting over activity in the motor system.

Bilateral high-frequency stimulation of the subthalamic nucleus (STN), commonly known as deep brain stimulation of the STN (STN-DBS), provides a significant improvement in cardinal motor symptoms and in the control of drug-induced complications of Parkinson's disease. To be clinically effective, stimulation of the STN must be applied at frequencies greater than 100 Hz, and electrostimulation is usually delivered at 130 Hz. Effective stimulation was shown to be associated with a significant decrease in the activity of the ipsilateral primary sensorimotor cortex at rest and a significant increase in premotor, anterior cingulate, pre-supplementary motor areas (pre-SMAs) and dorsolateral prefrontal cortices during movement. However, the process of deep brain stimulation of the subthalamic nucleus requires a neurosurgery, which involves electrodes being placed into the subthalamic nucleus region which includes a map of muscles of the human body, which is an extremely invasive intervention for the Parkinson's patient. In addition, axial symptoms, such as postural instability and gait difficulty (PIGD), freezing of gait, and impaired speech, have been reported to be resistant to STN-DBS and levodopa treatments (Cakmak, et al. Front Hum Neurosci 2017. 11:338).

It is known that surgical device applications are likely to have side effects. Moreover, the battery of the stimulator is placed under the thorax skin while the electrodes inserted into the brain tissue and the wires go under the skin. The frequency and the intensity of these stimulators can be altered wirelessly with an external unit. Therefore, in order to stimulate the STN externally, a nerve which is related with muscle innervation should be stimulated.

Among others, a prior art publication in the technical field of the stimulation device and system may be referred to as US 2016/151628 which discloses a method for stimulating the vagus nerve that lies under the skin of the subject's neck. The method comprises contacting the outer skin surface of the neck of the patient with a nerve stimulator and transmitting, via the nerve stimulator, electrical impulses sufficient to modulate the nerve non-invasively through the outer skin surface to the vagus nerve of the patient, wherein the one or more electrical impulses are generated and measuring the physiological response directly associated with modulation of the vagus nerve to detect whether the electrical impulses are being transmitted to the vagus nerve.

Another reference can be given as US 2013/225954, which discloses a device and method for treating a subject with dysphagia or other neurological disease. The device comprises a vibrotactile stimulator for applying at least one stimulus to the outside surface of a subject's neck; a connector for attaching the vibrotactile stimulator to an outside surface of the subject's neck, and a switch control communicatively connected to the vibrotactile stimulator to selectively engage a manual stimulation module and/or automatic stimulation module. Stimulation of an outside surface of the throat area of a subject by the stimulation device and system stimulates a swallowing reflex in the subject.

Another reference can be given as US 2019/209841, which discloses devices, systems and methods that allow a patient to self-treat a medical condition, such as migraine headache, by electrical noninvasive stimulation of a vagus nerve. The system comprises a handheld stimulator that is applied to the surface of the patient's neck, wherein the stimulator comprises or is joined to a smartphone. A camera of the smartphone may be used to position and reposition the stimulator to a particular location on the patient's neck.

Upper facial muscles around the orbital region are controlled bilaterally by the motor cortex through the facial nerve. In addition, unilateral STN-DBS has been demonstrated to induce strictly contralateral motor-evoked potentials in the trapezius, deltoid, biceps, and thenar muscles; however, the same stimulus reportedly always induces bilateral motor-evoked potentials in the orbicularis oculi, orbicularis oris, masseter, and sternocleidomastoid in Parkinson's patients (Cakmak, et al. Front Hum Neurosci 2017. 11:338).

The sternocleidomastoid muscle (SCM) is one of more than 20 pairs of muscles that act on the neck. SCM has a dual-innervation and multiple functions. SCM plays an important role in the posture of the neck and the body. It has been shown that a stimulation of the vestibular area electrically activates the sternocleidomastoid with evidence of a close connection between the vestibular area and the motoneurons of the SCM. The sternocleidomastoid is innervated by the spinal accessory nerve of the same side. It supplies only motor fibres. The cervical plexus supplies sensation, including proprioception, from the ventral primary rami of C2 and C7 (Bordoni and Varacallo. "Anatomy, Head and Neck, Sternocleidomastoid Muscle." StatPearls [Internet]. StatPearls Publishing, 2018). The anastomoses from C1 to spinal accessory nerve are also documented (Waxenbaum and Bordoni B. "Anatomy, Head and Neck, Cervical Nerves." StatPearls [Internet]. StatPearls Publishing, 2019).

Stimulation of the SCM with anterior/middle scalene muscles as the neck muscles is capable of modulation of the mesencephalic locomotor region. The cervical spinal nerves are capable of stimulation of the locus coeruleus antidromically via cervical sympathetic chain connections. The sympathetic component of the four cervical sensory nerves (lesser occipital nerve-originating at the C1, C2, C3, C4 spinal cord segments, greater auricular nerve originating at the C2-C3 spinal cord segments, transverse cervical nerve originating at the C2, C3 spinal cord segments and supraclavicular nerve originating at the C3, C4 spinal cord segments) relays to the cervical sympathetic chain and then to the nucleus tractus solitarius via locus coeruleus. The modulation of these centers (mesencephalic locomotor region, nucleus tractus solitarius and locus coeruleus) are found to be significant in improving autonomic system related functions but also the locomotion in PD (Cakmak, et al. Front Hum Neurosci 2017. 11:338). In addition to locomotion, stimulation of locus coeruleus and nucleus tractus solitarius via cervical nerves is capable of alleviating the conditions related with autonomic dysfunctions related with these nuclei dysfunctions such as migraine, epilepsy, irritable bowel syndrome, rheumatoid arthritis, opioid withdrawal and blood pressure regulation.

In light of this, a stimulation device and system is disclosed for placement on the neck of a subject, wherein said stimulation device is capable of stimulating the SCM muscles (and therefore stimulate the spinal accessory nerve which innervates SCM) as well as all the trunks of the cutaneous nerve branches (lesser occipital nerve-originating at the C1, C2, C3, C4 spinal cord segments, greater auricular nerve originating at the C2-C3 spinal cord segments, transverse cervical nerve originating at the C2, C3 spinal cord segments and supraclavicular nerve originating at the C3, C4 spinal cord segments) that emerge in the same zone known at the posterior border and midpoint of the SCM known as nerve punctum, so that the stimulation device can synchronously stimulate almost all the main sensory fibers and autonomic fibers of these nerves before they distribute to the neck skin and give their branches. In addition, the combined and synchronous effect of stimulation of the mesencephalic locomotor regions via SCM stimulation and also the locus coeruleus and nucleus tractus solitarius via the autonomic fibers of the cervical sensory nerves provide both motor and autonomic regulation. Synchronous stimulation of all four cervical sensory nerves (lesser occipital nerve, greater auricular nerve, transverse cervical nerve and supraclavicular nerve) provides the strongest antidromic neural connection to stimulate the cervical sympathetic ganglions that can be achieved from the human skin from a single point.

In this manner, said stimulation device is capable of alleviating both the autonomic and motor symptoms related to Parkinson disease, migraine, movement disorders, depression or pain management and blood pressure regulation as mentioned above, as well as other conditions and diseases that require autonomic regulation from a single stimulation region.

Features of the Stimulation Device and System

A feature of the stimulation device and system is to provide a stimulation device where the SCM muscles as well as all the trunks of the cutaneous nerve branches (lesser occipital nerve, greater auricular nerve, transverse cervical nerve and supraclavicular nerve) are stimulated transcutaneously by which treatment of neurological diseases such as Parkinson disease, migraine, movement disorders, depression or pain management and blood pressure regulation can be achieved.

Another feature of the stimulation device and system is to provide a stimulation device where the SCM muscles as well as all the trunks of the cutaneous nerve branches (lesser occipital nerve, greater auricular nerve, transverse cervical nerve and supraclavicular nerve) are stimulated synchronously from a single location in a non-invasive manner via the neck of the subject.

Another feature of the stimulation device and system is to provide a stimulation device where the stimulation parameters of the SCM muscles as well as all the trunks of the cutaneous cervical nerve branches (lesser occipital nerve, greater auricular nerve, transverse cervical nerve and supraclavicular nerve) are changed according to the data collected by a plurality of peripheral sensing units.

Another feature of the stimulation device and system is to provide a stimulation device where the SCM muscles as well as all the trunks of the cutaneous nerve branches (lesser occipital nerve, greater auricular nerve, transverse cervical nerve and supraclavicular nerve) are stimulated unilaterally by one stimulation device or bilaterally (synchronously or alternating with respect to each other) by two stimulation devices in communication with each other which can be placed on both sides of the subject's neck.

Another feature of the stimulation device and system is to provide wherein synchronous stimulation of cervical sensory nerves relays to the cervical sympathetic ganglia via sympathetic component of these sensory nerves, and then it relays to the nucleus tractus solitarius via locus coeruleus so that the stimulation can modulate autonomic activity.

BRIEF DESCRIPTION OF THE TECHNICAL DRAWINGS

Accompanying drawings are given solely for the purpose of exemplifying a stimulation device, whose advantages over prior art were outlined above and will be explained in brief hereinafter.

The drawings are not meant to delimit the scope of protection as identified in the Claims, nor should they be referred to alone in an effort to interpret the scope identified in said Claims without recourse to the technical disclosure herein.

FIG. 1 demonstrates a side view of the anatomy of the neck and positioning of a stimulation device according to an embodiment.

Figure 2:
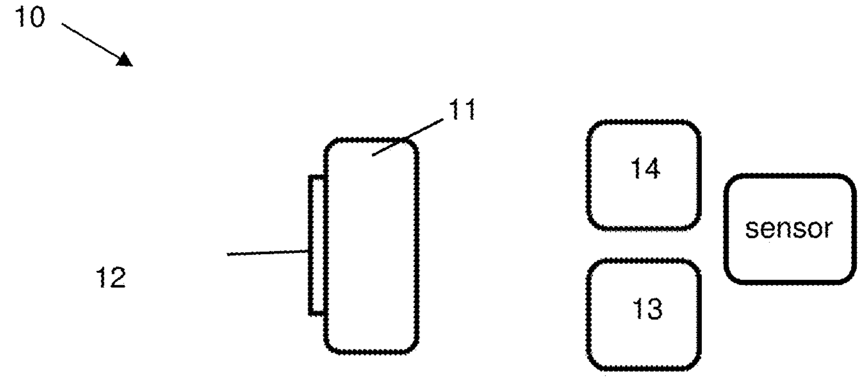

FIG. 2 demonstrates a schematic view of a stimulation device according to an embodiment.

Figure 3A:
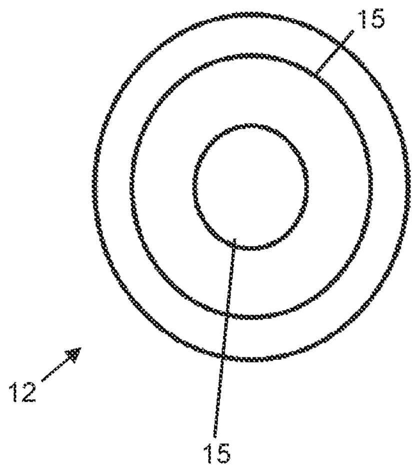

FIG. 3A demonstrates a schematic view of a first example alternative electrode configuration according to an embodiment.

Figure 3B:
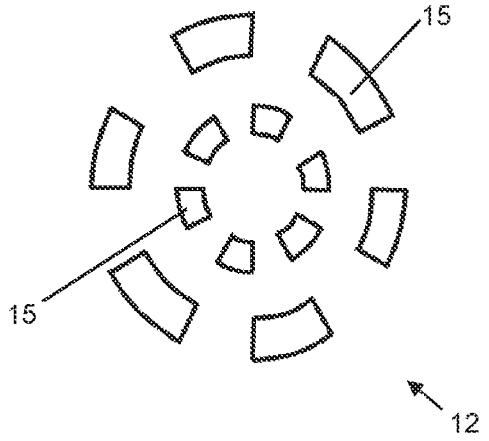

FIG. 3B demonstrates a schematic view of a second example alternative electrode configuration according to an embodiment.

DETAILED DESCRIPTION

The following numerals are referred to in the detailed description:

10 Stimulation device
11 Body
12 Stimulation means
13 Communication unit
14 Control unit
15 Electrode FIG. 1 illustrates a side view of the anatomy of the neck of a human, wherein SCM and cutaneous nerves can be seen. Cervical cutaneous nerves of the first four cervical nerves (C1-C4) have also sympathetic components via cervical sympathetic chain. This group of nerves is found deep to the SCM and comprises of both sensory and motor nerves. The branches of the cervical plexus emerge from the posterior triangle of the neck at nerve punctum. This point is found midway along the posterior border of the sternocleidomastoid muscle and approximately 2-3 cm superior to the clavicle. The cervical plexus has cutaneous and muscular branches. The cutaneous branches are the lesser occipital nerve, transverse cutaneous (cervical) nerve of neck, great auricular nerve, and the supraclavicular nerves that emerges at the nerve punctum (Rea, Paul. Essential clinically applied anatomy of the peripheral nervous system in the head and neck. Academic Press, 2016).

Presently disclosed is a stimulation device (10) connected to at least one sensor, having a body (11) whereby said device is attached to a subject, a communication unit (13) or communication circuitry, a control unit (14) or controller circuitry and at least one stimulation means (12), a stimulation end of which controlling the stimulation process based on the collected data, also through said stimulation device (10) as will be delineated hereinafter (FIG. 2).

The stimulation device (10) provides that fine-tuning of parameters such as current, voltage, polarization, signal form is carried out. The at least one stimulation means (12) of the stimulation device (10) is adapted to be transcutaneously attached to the neck of a subject at the location showed in FIG. 1, namely SCM as well as all the trunks of the cutaneous nerve branches (lesser occipital nerve, greater auricular nerve, transverse cervical nerve and supraclavicular nerve) that emerges in the same zone known at the posterior border and midpoint of the SCM as known as nerve punctum. Therefore, said stimulation device (10) can stimulate almost all the main sensory and autonomic fibers of these nerves before they distribute to the neck skin and give their branches. The stimulation device (10) is also capable of synchronously stimulating all of the C1- to $7^{th}$ cervical spinal nerves via the cutaneous nerves and the spinal accessory nerve (SCM stimulation) branches and their anastomoses from a single region. In addition, it can also modulate the cervical sympathetic ganglia and cervical sympathetic chain (and connected higher autonomic centers) via the cervical sympathetic nerves contribution to these cervical cutaneous nerves.

Said stimulation means (12) can deliver stimulation in the form of electrical (AC/DC) stimulation and/or a vibration and/or thermal and/or mechanical, and/or magnetic and/or optical and/or infrared, and/or any other method known in the art. In one embodiment, a laser can be used as an optical, mechanical and thermal stimulation means. In another embodiment, an infrared stimulation means utilizing different wavelengths can be used to provide optical and thermal stimulation. In another embodiment, thermal stimulation can be provided by discs capable of producing heat on the stimulation location and thermal stimulation can be realized by varying the temperature of the disc during operation. Preferably, said stimulation means (12) is at least one electrode (15) whereby stimulation is delivered in the form of electric impulses.

According to a first embodiment, stimulation device (10) comprises a body (11), which contains at least one electrode (15). Electrodes (15) are placed to provide stimulation to SCM as well as all the trunks of the cutaneous nerve branches as defined above. FIGS. 3A and 3B illustrate exemplary electrode (15) configurations. Different configurations may serve different purposes. For example an electrode (15) array as depicted in FIG. 3B can be used to provide stimulation predominantly to SCM. However, the person skilled in the art will appreciate that any configuration of electrodes (15) can be used in stimulation device (10). Electrodes (15) may be activated simultaneously, alternatively or in a synchronized manner.

In one embodiment, a control unit (14) or controller circuitry is placed in body (11) of said stimulation device (10). In yet another embodiment, a communication unit/circuitry (13) placed in body (11) of said stimulation device (10) is in wireless communication with an external control unit (14) and provides a certain parameter signal as voltage or current signal and preferable in the form of current-amplified signal to said at least one stimulation means (12). Said control unit (14) may operate in an open loop or a closed loop system. In the open loop system, the voltage and frequency of the stimulation signal is determined by user-entered parameters. In the closed loop system, the voltage and frequency of the stimulation signal is determined by the feedback from physiological sensors, such as an accelerometer, blood pressure, blood flow, skin color, skin electrical conductance or skin temperature sensors or a video capturing peripheral that collects blinking data or EMG, EEG or ECG or any other physiological sensors known in the art.

In a variation, stimulation device (10) may comprise a system that selectively varies specific operational parameters according to different symptoms in the same session. Generally, while the frequency signal set at 60 Hz cures the voice-related parameters (basically voice quality) of a subject, 130 Hz cures the rigidity and postural instability and 10 Hz can modulate sympathetic nerve activity. Therefore, according to the stimulation device and system, data collected from a plurality of sensors such as for instance an inertial measurement unit being embodied in peripheral sensing units in signal communication with the control unit of the present stimulation device (10), can be used in selectively applying varying treatment parameters. Likewise, the intensity, speed and for instance swallowing duration, etc., of a subject can be analyzed by a speech processing software (preferably real-time or as a pre-treatment recorded sample) and the data collected as such can thereby be used in selectively applying varying treatment parameters as explained above. Different treatment routines with varying frequencies can be subsequently applied in the manner that while a frequency value is adopted for a predetermined time duration, the frequency can be subsequently varied for another predetermined time duration in a symptom-specific manner.

In one embodiment, stimulation device (10) comprises at least one communication unit (13), which enables realizing of communication with other devices. Typically, control unit (13) enables signals to be sent to/received from stimulation means (12), controlling the driving circuit, receiving signals from the stimulating end and controlling the communication unit.

A video capturing peripheral can enable receiving of images from the subject and hence enabling visual monitoring of symptoms such as tremors. The received images are then processed by known image processing techniques and information such as intensity of tremors is acquired.

Alternatively, an inertial measurement unit as a peripheral unit with an stretch sensor and/or accelerometer and/or gyroscope can be placed on the subject, the activity of which is to be periodically monitored. Therefore, the intensity of disturbances can be sensed by measuring the acceleration of the body and filtering out signals coming from the head and the neck. Upon measurement of the disturbance level, the stimulation signal can be adjusted to target the specific needs of a subject, i.e., so as to be adapted to the changing state of the subject.

The adjustments to the stimulation signal can typically be carried out by changing the amplitude, frequency, pulse width, and pulse shape such as the harmonic content of the periodic pulses, etc. The phases of the stimulating devices relative to each other can be adjusted if a multitude of stimulating devices are used.

The stimulation device (10) typically comprises a communication unit/circuitry (13) in signal communication with the electronic control module (14), enabling communication with other devices such as remote control units, computers, peripheral measurement/sensor units, etc. The communication unit (13) conventionally supports known communication protocols/standards (IR, USB, IEEE 802 family, Bluetooth, RF communication interface, RS-232, RS-422, RS-485, SPI (serial peripheral interface) i2c, as well as proprietary interfaces and/or protocols, etc.).

The driving circuit typically enables increased driving power levels. Therefore, power can be fed to the electrodes (15) by the driving circuit.

In a preferred embodiment, different stimulating signal parameters (voltage, current, signal period, polarization and signal form) can be adjusted and the signal produced by the control unit may have a voltage of 0 V-15 V and the frequency of 2 Hz-250 Hz. The parameters of the stimulating signal can be automatically changed by the control unit depending on the situation of the subject or they can be remotely changed via a remote unit by an authorized user such as a physician, upon evaluating the situation of the subject. The frequency of the stimulation signals being generated is preferably between 2-250 Hz. It is worthy of note that lower limit of said frequency is selected as 2 Hz because 2 Hz is found to be a frequency value that induces peripheral nerve regeneration by protecting and regenerating the biological stimulation pathway.

In a preferred embodiment, the intensity of the stimulation can be altered in order to stimulate deep muscles fibers of SCM and anterior and middle scalene muscles or it can be kept at a lower intensity to stimulate predominantly the superficial cutaneous nerves that are described above.

The stimulation devices (10) can work as a single unit when placed unilaterally. In a variation of the stimulation device and system, two stimulation devices (10) are placed on either side of the subject's neck and work bilaterally (synchronously or alternating with respect to each other) in communication with the other stimulator via their communication units (13) in order to synergistically induce positive results associated with the treatment. The stimulation devices (10) are also capable of alternating the intensity of the stimulus on each side (when used bilaterally) independently in the context of the feedback data.

In a further variation of the stimulation device and system, stimulation device (10) also monitors frequency and wavelength of the applied voltage or current electrical signal through the driving circuit, which is advantageous in that the driving circuit in electrical connection with a feedback loop ensures that no variations occur in the stimulation signal during the stimulating states of subsequent periods of the stimulation signal.

In a further variation of the stimulation device and system, the control unit (14) is preferably integral with stimulation device (10) and can be controlled by a remote terminal through an appropriate software module to adjust parameters of the stimulation procedure.

In a further variation of the stimulation device and system, the stimulation signal can include signal components in the bursting frequencies. As is known to the skilled worker, bursting is a phenomenon of neuron activation patterns where periods of rapid action potential spiking are followed by resting phase periods.

In one embodiment, a stimulation device (10) comprising a body (11) the surface of which contains at least one stimulation means (12) and adapted to be transcutaneously attached to the neck of a human is proposed.

In a further embodiment, said stimulation means (12) is adapted to generate a stimulating signal during a stimulating state in the manner that said stimulation means (12) is positioned to be in stimulating contact with the sternocleidomastoid muscle and the trunks of four cervical cutaneous nerves, namely the lesser occipital nerve, greater auricular nerve, transverse cervical nerve or supraclavicular nerve, and their sympathetic axon contents which originate from the cervical sympathetic ganglia.

In a further embodiment, said stimulating means (12) comprises means of stimulation via electrical, optical (laser), infrared, vibrational, thermal, mechanical and/or magnetic stimulation.

In a further embodiment, said stimulating means (12) are activated simultaneously, alternatingly or in a synchronized manner.

In a further embodiment, said stimulating means (12) comprises at least one electrode (15).

In a further embodiment, said stimulating means (12) comprises an array of electrodes (15).

In a further embodiment, said stimulating means (12) comprises an array of electrodes (15) at predetermined points based on the innervation map of the neck in stimulating contact with the sternocleidomastoid muscle and the trunks of the lesser occipital nerve, greater auricular nerve, transverse cervical nerve or supraclavicular nerve.

In a further embodiment, said stimulation means (12) is configured to be directly attached to the neck so as to establish a direct contact relation therewith.

In a further embodiment, said stimulation device (10) comprises a control unit (14) and a communication unit (13).

In a further embodiment, said control unit (14) of said electro device (10) is configured to gradually change the stimulating signal applied by the stimulation means (12) in response to signals transmitted from a sensor unit.

In a further embodiment, said sensor unit is an accelerometer or a video capturing peripheral that collects blinking activity, pupil size data, skin color, skin impedance changes, skin temperature changes, blood flow/pressure changes or EMG, EEG or ECG, including optical sensors based ECG recorders and index derivatives of EMG, EEG or ECG data including Heart Rate Variability (HRV).

In a further embodiment, values of stimulating signal parameters are selectively varied according to data collected by at least one of sensing units including an inertial measurement unit, a voice recording unit or an image capturing unit.

In a further embodiment, said control unit (14) processes data collected by the video capturing peripheral such that natural blinking movements are differentiated from blinking movements induced by the stimulating signal whereby at least one threshold value of the stimulating signal is determined in view of the natural blinking movements being ignored.

In a further embodiment, the inertial measurement unit with an accelerometer in signal communication with the control unit is provided to collect movement data from a human body.

In a further embodiment, a voice recording unit in signal communication with the control unit is provided to monitor voice parameters including intensity, speed and swallowing duration of a patient.

In a further embodiment, voice parameters including intensity, speed and swallowing duration are analyzed real-time or as a pre-recorded sample.

In a further embodiment, an image capturing unit in signal communication with the control unit (14) is provided to capture images from different body portions or extremities of a patient to detect symptoms such as tremors.

In a further embodiment, the intensity, speed and swallowing duration values are analyzed by a speech processing software.

In a further embodiment, said stimulation device (10) is configured to provide to a subject unilateral or bilateral stimulation of sternocleidomastoid muscle and the trunks of the lesser occipital nerve, greater auricular nerve, transverse cervical nerve or supraclavicular nerve and their sensory and autonomic components.

In a further embodiment, two stimulation devices (10) are operable in a simultaneous manner in the manner that the stimulating signal generated during a stimulating state is applied by said two stimulation devices (10) at both sides of the neck in a synchronized manner.

In a further embodiment, stimulation device (10) comprises a temperature sensor such that temperature of the stimulation means (12) is continuously monitored to avoid excessive heating thereof beyond a predetermined limit.

In a further embodiment, said stimulation device (10) is operated such that the stimulation means' (12) initial temperature and temperature thereof at the end of a predetermined inactive period prior to the stimulation are monitored and the active state temperature of the stimulation means (12) is intermittently decreased to the temperature of a respective neck region as measured at the end of the predetermined inactive period of the stimulation end.

The methods, devices, processing, circuitry, and logic described above may be implemented in many different ways and in many different combinations of hardware and software. For example, all or parts of the implementations may be circuitry that includes an instruction processor, such as a Central Processing Unit (CPU), microcontroller, or a microprocessor; or as an Application Specific Integrated Circuit (ASIC), Programmable Logic Device (PLD), or Field Programmable Gate Array (FPGA); or as circuitry that includes discrete logic or other circuit components, including analog circuit components, digital circuit components or both; or any combination thereof. The circuitry may include discrete interconnected hardware components or may be combined on a single integrated circuit die, distributed among multiple integrated circuit dies, or implemented in a Multiple Chip Module (MCM) of multiple integrated circuit dies in a common package, as examples.

Accordingly, the circuitry may store or access instructions for execution, or may implement its functionality in hardware alone. The instructions may be stored in a tangible storage medium that is other than a transitory signal, such as a flash memory, a Random Access Memory (RAM), a Read Only Memory (ROM), an Erasable Programmable Read Only Memory (EPROM); or on a magnetic or optical disc, such as a Compact Disc Read Only Memory (CDROM), Hard Disk Drive (HDD), or other magnetic or optical disk; or in or on another machine-readable medium. A product, such as a computer program product, may include a storage medium and instructions stored in or on the medium, and the instructions when executed by the circuitry in a device may cause the device to implement any of the processing described above or illustrated in the drawings.

The implementations may be distributed. For instance, the circuitry may include multiple distinct system components, such as multiple processors and memories, and may span multiple distributed processing systems. Parameters, databases, and other data structures may be separately stored and managed, may be incorporated into a single memory or database, may be logically and physically organized in many different ways, and may be implemented in many different ways. Example implementations include linked lists, program variables, hash tables, arrays, records (e.g., database records), objects, and implicit storage mechanisms. Instructions may form parts (e.g., subroutines or other code sections) of a single program, may form multiple separate programs, may be distributed across multiple memories and processors, and may be implemented in many different ways. Example implementations include stand-alone programs, and as part of a library, such as a shared library like a Dynamic Link Library (DLL). The library, for example, may contain shared data and one or more shared programs that include instructions that perform any of the processing described above or illustrated in the drawings, when executed by the circuitry.

In some examples, each unit, subunit, and/or module of the system may include a logical component. Each logical component may be hardware or a combination of hardware and software. For example, each logical component may include an application specific integrated circuit (ASIC), a Field Programmable Gate Array (FPGA), a digital logic circuit, an analog circuit, a combination of discrete circuits, gates, or any other type of hardware or combination thereof. Alternatively or in addition, each logical component may include memory hardware, such as a portion of the memory, for example, that comprises instructions executable with the processor or other processors to implement one or more of the features of the logical components. When any one of the logical components includes the portion of the memory that comprises instructions executable with the processor, the logical component may or may not include the processor. In some examples, each logical components may just be the portion of the memory or other physical memory that comprises instructions executable with the processor or other processor to implement the features of the corresponding logical component without the logical component including any other hardware. Because each logical component includes at least some hardware even when the included hardware comprises software, each logical component may be interchangeably referred to as a hardware logical component.

A second action may be said to be "in response to" a first action independent of whether the second action results directly or indirectly from the first action. The second action may occur at a substantially later time than the first action and still be in response to the first action. Similarly, the second action may be said to be in response to the first action even if intervening actions take place between the first action and the second action, and even if one or more of the intervening actions directly cause the second action to be performed. For example, a second action may be in response to a first action if the first action sets a flag and a third action later initiates the second action whenever the flag is set.

To clarify the use of and to hereby provide notice to the public, the phrases "at least one of <A>, <B>, . . . and <N>" or "at least one of <A>, <B>, . . . <N>, or combinations thereof" or "<A>, <B>, . . . and/or <N>" are defined by the Applicant in the broadest sense, superseding any other implied definitions hereinbefore or hereinafter unless expressly asserted by the Applicant to the contrary, to mean one or more elements selected from the group comprising A, B, . . . and N. In other words, the phrases mean any combination of one or more of the elements A, B, . . . or N including any one element alone or the one element in combination with one or more of the other elements which may also include, in combination, additional elements not listed.

While various embodiments have been described, it will be apparent to those of ordinary skill in the art that many more embodiments and implementations are possible. Accordingly, the embodiments described herein are examples, not the only possible embodiments and implementations.

The invention claimed is:

1. A stimulation device comprising: a body having a surface, the surface including at least one stimulation means adapted to be transcutaneously attached to a neck of a human at the nerve punctum; wherein said stimulation means is adapted to generate a stimulating signal during a stimulating state wherein said stimulation means is configured to synchronously stimulate from a single position a sternocleidomastoid muscle and trunks of a plurality of cervical cutaneous nerves, the cervical cutaneous nerves comprising a lesser occipital nerve, a greater auricular nerve, a transverse cervical nerve, and a supraclavicular nerve, each of the cervical cutaneous nerves including sympathetic axon contents which originate from a respective cervical sympathetic ganglia; and wherein said stimulation device further comprises a controller circuitry and a communication circuitry, said controller circuitry configured to change the stimulating signal applied by the stimulation means in response to sensor data signals transmitted from a sensor, wherein said sensor comprises a video capturing peripheral that collects blinking activity; and wherein said controller circuitry is further configured to process the sensor data signals collected by the video capturing peripheral to differentiate natural blinking movements from blinking movements induced by the stimulating signal, and to control at least one threshold value of the stimulating signal in response to the blinking movements induced by the stimulating signal, and the natural blinking movements being ignored.

2. The stimulation device as set forth in claim 1, wherein said stimulating means comprises means of stimulation via at least one of electrical, optical, infrared, vibrational, thermal, mechanical or magnetic stimulation.

3. The stimulation device as set forth in claim 2, wherein said stimulating means comprises two or more stimulating means activated simultaneously, alternatingly or in a synchronized manner to provide the means of stimulation via at least one of electrical, optical, infrared, vibrational, thermal, mechanical or magnetic stimulation.

4. The stimulation device as set forth in claim 2, wherein said stimulating means comprises at least one electrode.

5. The stimulation device as set forth in claim 4, wherein said stimulating means comprises an array of electrodes.

6. The stimulation device as set forth in claim 5, wherein said stimulating means comprises an array of electrodes at predetermined points based on an innervation map of the neck in stimulating contact with the sternocleidomastoid muscle and the trunks of at least one of the lesser occipital nerve, the greater auricular nerve, the transverse cervical nerve or the supraclavicular nerve.

7. The stimulation device as set forth in claim 1, wherein said stimulation means is configured to be directly attached to the neck so as to establish a direct contact relation therewith.

8. The stimulation device as set forth in claim 1, wherein said sensor is further comprises a physiological sensor that collects pupil size data, skin color, skin impedance changes, skin temperature changes, or blood flow changes or an electromyography (EMG), an electroencephalogram (EEG) or an electrocardiogram (ECG) sensor.

9. The stimulation device as set forth in claim 1, wherein said controller circuitry is further configured to selectively vary values of stimulating signal parameters according to the sensor data signals collected by the sensor, the sensor further comprising an inertial measurement sensor, or a voice recording sensor.

10. The stimulation device as set forth in claim 9, wherein the sensor further comprises the inertial measurement sensor that includes an accelerometer to collect movement data from a human body of the human.

11. The stimulation device as set forth in claim 1, wherein the sensor further comprises a voice recording sensor in signal communication with the controller circuitry, the controller circuitry further configured to monitor voice parameters including intensity, speed and swallowing duration of a patient using the sensor data signals transmitted from the voice recording sensor.

12. The stimulation device as set forth in claim 11, wherein the controller circuitry is further configured to analyze the voice parameters including the intensity, speed and swallowing duration in real-time or as a pre-recorded sample.

13. The stimulation device as set forth in claim 1, wherein the sensor further comprises an image capturing sensor in signal communication with the controller circuitry, the image capturing sensor to capture images from different body portions or extremities of the human, and the controller circuitry further configured to detect symptoms such as tremors from the captured images from different body portions or extremities of the human.

14. The stimulation device as set forth in claim 11, wherein the controller circuitry is further configured to execute speech processing code stored in a memory, and the speech processing code is executable by the controller circuitry to analyze intensity, speed and swallowing duration values provided by the sensor data signals.

15. The stimulation device as set forth in claim 1, wherein said stimulating signal is configured to provide a unilateral or a bilateral stimulation of the sternocleidomastoid muscle and the trunks of at least one of the lesser occipital nerve, the greater auricular nerve, the transverse cervical nerve or the supraclavicular nerve and sensory and autonomic components thereof.

16. The stimulation device as set forth in claim 1, further comprising a temperature sensor, the controller circuitry further configured to monitor a temperature of the stimulation means to avoid excessive heating thereof beyond a predetermined limit.

17. The stimulation device as set forth in claim 16, wherein the controller circuitry is further configured to monitor an initial temperature of the stimulation means and a temperature of the stimulation means at an end of a predetermined inactive period prior to the stimulation state, and the controller circuitry is further configured to intermittently decrease an active state temperature of the stimulation means to a temperature of a respective neck region as measured at the end of the predetermined inactive period.

18. A stimulation system comprising: a plurality of stimulation devices; each of the stimulation devices including a body having a surface, the surface including at least one stimulation means adapted to be transcutaneously attached to a neck of a human at the nerve punctum; wherein said stimulation means is adapted to generate a stimulating signal during a stimulating state wherein said stimulation means is configured to synchronously stimulate from a single position a sternocleidomastoid muscle and trunks of a plurality of cervical cutaneous nerves, the cervical cutaneous nerves comprising a lesser occipital nerve, a greater auricular nerve, a transverse cervical nerve, and a supraclavicular nerve, each of the cervical cutaneous nerves including sympathetic axon contents which originate from a respective cervical sympathetic ganglia; and wherein at least two of the stimulation devices are operable in a simultaneous manner such that the stimulating signal generated by each of the at least two of the simulation devices during a stimulating state is respectively applied by said at least two of the stimulation devices at both sides of the neck in a synchronized or alternating manner; and wherein at least one of the stimulation devices further comprises a controller circuitry and a communication circuitry, said controller circuitry configured to change the stimulating signal applied by the stimulation means in response to sensor data signals transmitted from a sensor, wherein said sensor comprises a video capturing peripheral that collects blinking activity; and wherein said controller circuitry is further configured to process the sensor data signals collected by the video capturing peripheral to differentiate natural blinking movements from blinking movements induced by the stimulating signal, and to control at least one threshold value of the stimulating signal in response to the blinking movements induced by the stimulating signal, and the natural blinking movements being ignored.

* * * * *